United States Patent [19]

Davey

[11] Patent Number: 5,618,784

[45] Date of Patent: Apr. 8, 1997

[54] METHYLBUTOXY-PROPIONITRILES AND THEIR USE AS PERFUMES

[75] Inventor: Paul N. Davey, Willesborough, Great Britain

[73] Assignee: Quest International B.V., Naarden, Netherlands

[21] Appl. No.: 454,146

[22] PCT Filed: Dec. 2, 1993

[86] PCT No.: PCT/EP93/03417

§ 371 Date: Sep. 26, 1995

§ 102(e) Date: Sep. 26, 1995

[87] PCT Pub. No.: WO94/13626

PCT Pub. Date: Jun. 23, 1994

[30] Foreign Application Priority Data

Dec. 9, 1992 [EP] European Pat. Off. ............. 92311227

[51] Int. Cl.$^6$ ............. A61K 7/46; C07C 255/17
[52] U.S. Cl. ................. 512/6; 558/447
[58] Field of Search .................. 558/447; 512/6

[56] References Cited

U.S. PATENT DOCUMENTS 5,294,602  3/1994  Brunke et al. .............. 512/6

Primary Examiner—Johann Richter
Assistant Examiner—Ebenezer Sackey
Attorney, Agent, or Firm—Cushman Darby & Cushman IP Group Pillsbury Madison & Sutro LLP

[57] ABSTRACT

Novel compounds, 3-(2-methylbut-1-oxy)- and 3-(3-methylbut-1-oxy)-2-methylpropionitrile, use of these compounds as fragrance materials, and perfumes containing these compounds.

3 Claims, No Drawings

METHYLBUTOXY-PROPIONITRILES AND THEIR USE AS PERFUMES

This application is a 371 of PCT/EP93/03417 filed Dec. 2, 1993 and published as WO94/13626 Jun. 23, 1994.

The present invention relates to certain methylbutoxypropionitriles, to the use of these compounds as fragrance materials and to perfumes and perfumed products containing these compounds.

Many synthetic fragrance materials have been developed, especially in the last decades to substitute known perfume materials of natural origin. Nevertheless there is a constant need for new synthetic fragrance materials which are more stable than those previously developed and/or have additional or more delicate odour notes to further complete the fragrance palette from which the perfumer can chose in composing perfumes which are suitable also for various aggressive environments.

Various aliphatic and aromatic nitriles are known in the art of perfumery. They were developed because of their good stability in aggressive media and their general odour similarity with the corresponding aldehydes, many of which were already used in perfumery before the development of the nitriles. Various examples are described in S. Arctander, Perfume and Flavor Chemicals (Montclair, N.J., 1969). Certain ether-nitriles have been described in the art. They were prepared by addition of aliphatic alcohols to acrylonitrile, methacrylonitrile or crotonnitrile. The ether-nitriles are reported to have odours reminiscent of the alcohols from which they were prepared. Thus, J. Kulesza et al, Riechstoffe, Aromen, Körperpflegemittel. Nr. 2/75, pages 34, 37 describe a series of addition products of alcohols to acrylonitrile. From the odour decriptions it is clear that the odours of most ether-nitriles are similar to those of the corresponding alcohols. Similarly, in DE-A-2601825 the addition products of various saturated and unsaturated aliphatic alcohols to acrylonitrile have been described as possibly of interest in perfumery and as polar solvents.

Although this reference gives very little information on the actual odours of the compounds, it does say that the odour is determined, at least in part, by the corresponding alcohol. The odour of 3-methylbut-3-en-1-oxy-propionitrile is decribed as mainly fruity, green. No further particulars or examples of any use of the compounds in perfumery are given. Finally, in EP-A-0 491 127 various hexenyloxy-propionitriles and hexenyloxy-methylpropio-nitriles are described as having predominantly green odour notes.

It has now been found that 3-(2-methylbut-1-oxy)- and 3-(3-methylbut-1-oxy)-2-methylpropionitrile, of which the formulae are presented below, are valuable fragrance materials with jasmine-type odours with lactonic notes.

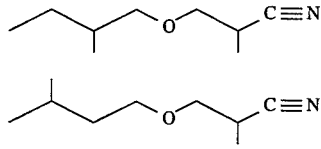

The olfactive properties of the compounds of the invention are thus surprisingly different from what might have been expected from the prior art in that they are not reminiscent of the corresponding alcohols, which both have a pungent and from a perfumery point of view useless odour. Also, the olfactive properties of the compounds of the invention are very different from those of the ether-nitriles of the prior art.

The ether-nitriles according to the invention are not only novel as perfume components, they are also novel as such. They may be prepared according to methods known in the art for similar compounds, such as described by J. H. MacGregor and C. Pugh, J. Chem Soc., 535 [1945], or as decribed in DE-A-2 121 325, DE-A-2 217 494 or EP-A-0 491 127.

The ether-nitriles according to the invention are powerful fragrance materials which may be used as such to impart, strengthen or improve a jasmine odour note in products, or they may be used as a component of a perfume to impart, strengthen or improve a jasmine note therein. For the purposes of this invention a perfume is intended to mean a mixture of fragrance materials, if desired mixed with or dissolved in a suitable solvent or mixed with a solid substrate, which is used to impart a desired odour to the skin and/or all types of products. Examples Of such products are: fabric washing powders and liquids and other fabric care products; detergents and household cleaning, scouring and disinfection products; air fresheners, room sprays and pomanders; candles; soaps, shampoos and other personal cleaning products; cosmetics such as creams, ointments, toilet waters, preshave-, aftershave- and other lotions, talcum powders, body deodorants and antiperspirants.

Fragrance materials which can be advantageously combined with the compounds according to the invention or the said organoleptic mixtures are, for example, natural products such as extracts, essential oils, absolutes, resinoids, resins, concretes etc., but also synthetic basic substances such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials - 1991" Allured Publishing Co Wheaton, Ill. USA.

Examples of fragrance materials which can be used in combination with the ether-nitriles according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenylcarbinyl acetate, p-tert-butylcyclohexyl acetate, isononyl acetate, vetiveryl acetate, vetiverol, 3-hexylcinnamaldehyde, 2-methyl-3-(p-tert-butylphenyl)propanal, 2-methyl-3-(p-isopropylphenyl)propanal, 3-(p-tert-butylphenyl)-propanal, tricyclodecenyl acetate, tricyclodecenyl propionate, 4-(4-hydroxy-4-methyl-pentyl)-3-cyclohexenecarbaldehyde, 4-(4-methyl-3-pentenyl)-3-cyclohexenecarbaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethyl-acetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxy-citronellal, ionones, methylionones, isomethylionones, irones, cis-3-hexenol and esters thereof, indan musks tetralin musks isochroman musks macrocyclic ketones, macrolactone musks ethylene brassylate, aromatic nitromusks.

Solvents which can be used in perfume compositions which contain compounds according to the invention are, for example: ethanol, isopropanol, diethyleneglycol monoethyl ether, dipropylene glycol, diethyl phthalate, triethyl citrate, etc.

The quantities in which the ether-nitriles according to the invention can be used in perfumes or in products to be perfumed may vary within wide limits and depend, inter alia, on the nature of the product, on the nature and the quantity of the other components of the perfume in which the compounds are used and on the olfactive effect desired. It is therefore only possible to specify wide limits, which, however, provide sufficient information for the specialist in the art to be able to use the ether-nitriles according to the invention for his specific purpose. In perfumes an amount of 0.01% by weight or more of the compounds according to the invention will generally have a clearly perceptible olfactive effect. Preferably the amount is 0.1% by weight and may be up to 80% by weight. The amount of ether-nitriles according to the invention present in products will generally be at least 0.1 ppm by weight.

The following examples are only intended to illustrate the preparation and use of the ether-nitriles according to the invention, but the invention is not in any way limited thereto

EXAMPLE 1

Preparation of ether-nitriles

The methylbutanol (0,34 mol) was put in a three-necked flask with potassium hydroxide catalyst (1 g). The methacrylonitrile (0,20 mol) was added dropwise over half an hour, the reaction being carried out under nitrogen. After addition, the mixture was heated to 50° C. and allowed to reflux for 1 hour. Most of the excess alcohol was removed using the rotary evaporator. The organic layer was extracted with cyclohexane (50 ml) in a separating funnel and then washed with hydrochloric acid (0,5M, 100 ml). The aqueous layer was run off and the remaining organic layer was washed with a second portion of hydrochloric acid and then with brine (100 ml). The organic layer was then dried over magnesium sulphate. After filtering off the magnesium sulphate and washing the filter paper with a little cyclohexane, the solvent was evaporated off using a rotary evaporator. Distillation was carried out under reduced pressure, the unreacted alcohol being the first fraction obtained, followed by the ether-nitrile, obtained as a colourless oil.

GC was done on a Vista 6000 Gas Chromatograph, using a packed. SE52 column, temperature programmed at 70°–240° C., rising 4° C./min. Retention times are given in minutes. $^1$H-NMR spectra were obtained in $CDCL_3$ as the solvent, using a Jeol GSX 400 MHz NMR spectrometer. TMS was used as an internal standard. Chemical shifts are given in ppm as δ values.

3-(2-Methylbut-1-oxy) -2-methylpropionitrile GC r.t.: 16.66; BP 78° C. at 0.01 kPa; $^1$H-NMR (400 MHz): 0.85 (m, 6H, 2Me), 1.15 (m, 1H), 1.3 (d, 3H, MeCHCN), 1.4 (m, 1H), 1.65 (m, 1H), 2.8 (m, 1H), 3.25–3.45 (m, 4H, $CH_2OCH_2$); Yield: 45%.

3-(3-Methylbut-1-oxy)-2-methylpropionitrile GC r.t.: 16.49; BP 60° C. at 0.01 kPa; $^1$H-NMR (400 MHz): 0.87 (d, 6H, 2Me), 1,28 (d, 3H, MeCHCN), 1,44 (q, 2H), 1,67 (m, 1H, MeCHME), 2.80 (m, 1H CHCN), 3.41–3.51 (m, 4H, $CH_2OCH_2$); Yield: 60%.

EXAMPLE 2

A chypre-type perfume for use in toilet soap was prepared according to the following recipe.

| | |
|---|---|
| Bergamot oil | 19,0 |
| α-Methyl ionone iso | 12,0 |
| P-tert-butyl-dihydrocinnamic aldehyde | 12,0 |
| Jasmin absolute | 10,0 |
| Coumarin | 7,0 |
| Amyl salicylate | 6,5 |
| Rosana extra A-118001 (Q) | 5,0 |
| Vetiver Bourbon | 5,0 |
| Ylang oil | 4,5 |
| Musk ambrette sub. AB 2002 (Q) | 4,0 |
| Patchouli oil acid washed | 3,0 |
| Clove stem oil | 3,0 |
| Undecalactone (10%)* | 2,5 |
| Dodecanal (50%)* | 1,0 |
| Treemoss absolute colourless | 1,0 |
| Cervolide (Q) | 1,0 |
| Civet AB 394A (Q) | 0,5 |
| Dipropylene glycol | 2,5 |
| 3-(3-Methylbut-1-oxy)-2-methylpropionitrile | 0.5 |
| Total | 100 |

*solution in dipropylene glycol
(Q) fragrance material marketed by Quest International, Ashford, Kent, U.K.

3-(3-Methylbut-1-oxy)-2-methylpropionitrile supports and strengthens the floral aspects of the above fragrance, in particular the Jasmin note.

I claim:

1. 3-(2-methylbut-1-oxy)-2-methylpropionitrile or 3-(3-methylbut-1-oxy)-2-methylpropionitrile.

2. Perfumes containing ether-nitriles characterized in that they contain one or both of 3-(2-methylbut-1-oxy)-2-methylpropionitrile or 3-(3-methylbut-1-oxy)-2-methylpropionitrile.

3. Perfumes according to claim 2 characterized in that they contain at least 0.01% by weight of the mentioned ether-nitriles.

* * * * *